United States Patent [19]

Oxman

[11] Patent Number: 5,849,813
[45] Date of Patent: Dec. 15, 1998

[54] OXIDATIVE PRETREATMENT FOR IMPROVED ADHESION

[75] Inventor: Joel D. Oxman, St. Louis Park, Minn.

[73] Assignee: Minnesota Mining and Manufacturing Company, St. Paul, Minn.

[21] Appl. No.: 14,104

[22] Filed: Feb. 5, 1993

[51] Int. Cl.$^6$ .................................................. A61K 5/01
[52] U.S. Cl. ..................... 523/116; 433/217.1; 433/219; 523/115
[58] Field of Search .................... 523/115, 116; 433/217.1, 219; 524/406, 418, 429, 435, 438, 439, 440

[56] References Cited

U.S. PATENT DOCUMENTS

| | | | |
|---|---|---|---|
| 3,513,123 | 5/1970 | Saffir | 260/37 |
| 3,574,943 | 4/1971 | Stark | 32/15 |
| 3,882,600 | 5/1975 | Plymale | 32/15 |
| 3,997,504 | 12/1976 | Plymale | 260/42.27 |
| 4,001,483 | 1/1977 | Lee, Jr. et al. | 536/270 |
| 4,064,629 | 12/1977 | Stoner et al. | 32/15 |
| 4,222,780 | 9/1980 | Shibatani et al. | 106/35 |
| 4,235,633 | 11/1980 | Tomioka et al. | 106/35 |
| 4,259,075 | 3/1981 | Yamauchi et al. | 433/217 |
| 4,259,117 | 3/1981 | Yamauchi et al. | 106/35 |
| 4,368,043 | 1/1983 | Yamauchi et al. | 433/217 |
| 4,383,052 | 5/1983 | Hige et al. | 523/118 |
| 4,499,251 | 2/1985 | Omura et al. | 526/278 |
| 4,514,342 | 4/1985 | Billington et al. | 260/952 |
| 4,515,930 | 5/1985 | Omura et al. | 526/276 |
| 4,537,940 | 8/1985 | Omura et al. | 526/278 |
| 4,539,382 | 9/1985 | Omura et al. | 526/276 |
| 4,544,467 | 10/1985 | Bunker et al. | 204/159.24 |
| 5,011,410 | 4/1991 | Culler et al. | 433/208 |
| 5,190,795 | 3/1993 | Culler | 427/226 |

FOREIGN PATENT DOCUMENTS

| | | |
|---|---|---|
| 0 058 483 | 1/1982 | European Pat. Off. . |
| 94101821 | 5/1994 | European Pat. Off. . |
| 2 561 521 | 3/1984 | France . |
| 57-143372 | 2/1981 | Japan . |
| 57-167364 | 4/1981 | Japan . |
| 63-175085 | 7/1988 | Japan . |
| 63-250310 | 10/1988 | Japan . |

OTHER PUBLICATIONS

M. Staninec and M. Holt, *Journal of Prosthetic Dentistry* (1988), vol. 59, pp. 397–402.

A. Lacey and M. Staninec, *Quintessence International* (1989), vol. 20, pp. 521–524.

Y. Aboush and C. Jenkins, *Br. Den. J.* (1989), vol. 166, pp. 255–257.

Y. Aboush and R. Elderton, *Dent. Mater.* (1991), vol. 7, pp. 130–132.

A. Ben–Amar, *J. Am. Dent. Assoc.* (1989), vol. 119, pp. 725–728.

M. Mitrosky, Jr., *Quintessence International* (1981), vol. 9, pp. 871–874.

H. J. Staehle et al., *Dtsch. Zhanartzt* (1988), vol. 43, pp. 952–957.

M. Buonocore, W. Wileman, and F. Brudevold, *J. Dent. Res.*, 35, 846 (1956).

M. Buonocore and M. Quigley, *J. Amer. Dent. Assoc.*, 57, 807 (1958).

M. Anbar and E. Farley, *J. Dent. Res.*, 53, 879 (1974).

E. Farley, R. Jones, and M. Anbar, *J. Dent. Re.*, 56, 1943 (1977).

J. A. Warren, Jr., and K.–J.M. Solderholm, *Dent. Mater.* (1988), vol. 4, pp. 191–196.

P. Mojon, E.B. Hawbolt, M.J. MacEntee and U.C. Belser, *J. Dent. Res.*, 68, 1545–1549 (1989).

A. Shimizu, T. Ui, and M. Kawakami, *Dent. Mater.* (1986), vol. 5, pp. 225–232.

Y. Torii, M. Staninec, M. Kawakami, S. Imazato, M. Torii, and Y. Tsuchitani, *Oper. Dent.* (1989), vol. 14, pp. 142–148.

Y. Aboush and R. Elderton, *Br. Dent. J.*, (1991), 170, pp. 219–222.

*Primary Examiner*—Paul R. Michl
*Attorney, Agent, or Firm*—F. Andrew Ubel

[57] ABSTRACT

This invention provides an adhesion promoter composition, comprising: a primer composition comprising an oxidant having an oxidation potential greater than the absolute value of the $E^O$ reductant of the adherend and optionally a solvent; and an adhesive composition.

This invention also provides a method of adhering a restorative material to an amalgam substrate, comprising the steps of: applying a primer composition and an adhesive to an amalgam substrate; hardening the adhesive; and optionally overcoating the adhesive with a restorative material.

These methods and materials have utility for applications that require adhesion to existing dental amalgams including, for example, the esthetic veneering of an amalgam restorative with a composite restorative material, and the repair or modification of old amalgam restorations with a fresh amalgam or with a composite restorative material.

38 Claims, No Drawings

OXIDATIVE PRETREATMENT FOR IMPROVED ADHESION

TECHNICAL FIELD

This invention relates to primers and adhesives for adhering to dental metal, e.g., dental amalgam, as well as to methods of using such primers and adhesives.

BACKGROUND ART

Dental amalgams and restoratives are used extensively for intracoronal and extracoronal restorations. Amalgam, however, is a difficult material to adhere to. For example, dental amalgam does not adhere to tooth structure, therefore, the dentist must prepare the tooth cavity with dovetails and various cutout grooves that mechanically lock the dental amalgam into the cavity. Such preparation, however, results in excavation of more tooth structure than would otherwise be necessary if there was good adhesion between the tooth structure and the dental amalgam. Moreover, leakage at the interface of the dental amalgam and cavity wall (known as "microleakage") tends to occur. This microleakage allows penetration of bacteria, soluble salts, and saliva into any space between the dental amalgam and tooth structure. This can lead to inflammation, pulp irritation, demineralization of the tooth, corrosion of the dental amalgam, and other attendant complications. An adhesive material to provide an improved seal between dental amalgam and tooth structure could minimize and/or prevent microleakage and allow for a stronger restoration due to excavation of less tooth material.

While these limitations have long been known, only recently has there been some success towards providing adhesives to achieve significant adhesion of freshly placed dental amalgam to hard tissue. Products claiming to make dental amalgam adhesive to tooth structure are available. One such product is sold in a kit under the trademark AMALGAMBOND™ Adhesive (Parkell Co.). This product is a liquid adhesive to be coated directly onto tooth structure. The active ingredients in the adhesive include 4-META (4-methacryloxyethyl trimellitic anhydride) and TBB (tri-n butyl borane). Other products which similarly involve coating a specific curable resin directly onto tooth structure to make dental amalgam adhere are available under the trademarks PANAVIA™ Dental Adhesive (Kuraray Company) and SUPERBOND™ Adhesive (Sun Medical Co., Ltd., Kyoto, Japan). These latter products are difficult to employ, since there are a number of required preparatory steps for their application and curing. Although the performance of these products is currently under investigation in a number of laboratories, it is presently believed that these products are of limited utility due to their complexity and less than ideal performance. Alternatively, simplified high performance dental amalgam adhesives (capable of providing substantial adhesion of freshly placed dental amalgam to hard tissue) have been disclosed in U.S. pending patent applications 07/815,171; 07/815,172; and 07/815,697 and published world patent application WO 92/11837.

Articles that describe bonding of dental amalgam to tooth structure by precoating the tooth with ethylenically unsaturated adhesive resin include M. Staninec and M. Holt, *Journal of Prosthetic Dentistry* (1988), Vol. 59, pp. 397–402, A. Lacey and M. Staninec, *Quintessence International* (1989), Vol. 20, pp. 521–524, Y. Aboush and C. Jenkins, *Br. Dent. J.* (1989), Vol. 166, pp. 255–257, Y. Aboush and R. Elderton, *Br. Dent. J.* (1991), Vol. 170, pp. 219–222, and Y. Aboush and R. Elderton, *Dent. Mater.* (1991), Vol. 7, pp. 130–132. The last article involves adhesion to previously hardened dental amalgam, whereas the other articles involve adhesion to fresh dental amalgam. Also, A. Ben-Amar, *J. Am. Dent. Assoc.* (1989) Vol. 119, pp. 725–728, describes a reduction in microleakage at the margins of dental amalgam restorations when "SCOTCHBOND" Dual Cure Dental Adhesive (3M) is applied to cavity margins prior to application of dental amalgam, and M. Mitrosky, Jr., *Quintessence International* (1981) Vol. 9, pp. 871–874, describes the use of ethyl cyanoacrylate as a bonding agent beneath dental amalgam and composite restoratives. H. J. Staehle et al., *Dtsch. Zahnartzt* (1988) Vol. 43, pp. 952–957, describes the use of various dental adhesives and varnishes to adhere dental amalgam to dentin.

Adhesive compositions that employ phosphorus-containing free-radically polymerizable compounds have been reported, see, e.g., M. Buonocore, W. Wileman, and F. Brudevold, *J. Dent. Res.*, 35, 846 (1956), M. Buonocore and M. Quigley, *J. Amer. Dent. Assoc.*, 57, 807 (1958), M. Anbar and E. Farley, *J. Dent. Res.*, 53, 879 (1974), E. Farley, R. Jones, and M. Anbar, *J. Dent. Res.*, 56, 1943 (1977), U.S. Pat. Nos. 3,882,600, 3,997,504, 4,222,780, 4,235,633, 4,259,075, 4,259,117, 4,368,043, 4,383,052, 4,499,251, 4,514,342, 4,515,930, 4,537,940, 4,539,382, and 4,544,467, European published patent application No. 0 058 483, and Japanese laid-open patent application (Kokai) Nos. 57-143372 and 57-167364.

The use of chemical primers and etchants as surface modifiers for promoting improved adhesion to a variety of dental substrates is well known. For example, dentin and enamel are commonly treated or etched with acidic primers, while porcelain surfaces are routinely treated with a silane coupling agent. In each case, the respective substrate is modified chemically with a specific treatment that results in enhanced adhesion between the substrate and the resin based adhesive.

Likewise, little success has been reported towards bonding dental composites to set dental amalgam. Typical approaches include roughening the dental amalgam surface with a burr (or via a micro-sandblasting technique) followed by the application of an adhesive. The surface modifications result in a textured surface yielding mechanically retained restorations or repairs with limited adhesion. The implications of limited adhesion to previously set dental amalgam include the inability to repair fractured dental amalgam with either new dental amalgam or a composite restorative and the inability to adhesively veneer dental amalgams with composite restorative materials.

SUMMARY OF THE INVENTION

This invention provides an adhesion promoting composition, comprising: a primer composition comprising an oxidant having an oxidation potential greater than the absolute value of the $E^o$ reductant of the adherend and optionally a solvent; and an adhesive composition. Preferably, the oxidant has an oxidation potential greater than about 0.8 Volts. This invention also provides a method of chemically treating a set amalgam surface with an oxidizing agent such that the modified surface exhibits improved adhesion to dental adhesive and restorative compositions.

This invention also provides a method of adhering a restorative material to an dental amalgam substrate, comprising the steps of:

applying a primer composition to an dental amalgam substrate;

applying an adhesive composition to the treated dental amalgam substrate;

hardening the adhesive; and optionally overcoating the adhesive with a restorative material.

These methods and materials have utility for applications that require adhesion to existing dental amalgams including, for example, the esthetic veneering of an dental amalgam restorative with a composite restorative material, and the repair or modification of old dental amalgam restorations with a fresh dental amalgam or with a composite restorative material.

In a preferred method of the invention, the primer is permitted to stand on the adherend for a desired period of time and then rinsed (e.g., by water rinsing) to leave a primed adherend, the adherend is overcoated with a layer of adhesive, then the adhesive is hardened and optionally overcoated with a composite or restorative (hereafter such composites and restoratives will be referred to collectively as "restoratives") or other hardenable coating. Thus, the invention enables priming of an adherend, such as dental amalgam, in order to improve the bond strength or durability of a restorative or coating applied thereto.

DETAILED DESCRIPTION OF THE INVENTION

This invention relates to a fast and easy method for achieving high bond strengths to previously set dental amalgam. I have discovered that the pretreatment of dental amalgam with a primer solution of an oxidant having a formal electrode potential ("$E^O$") greater than the absolute value of the $E^O$ reductant of the adherend, preferably greater than about 0.8 Volts, followed by the application of an adhesive, preferably a dental adhesive, results in enhanced adhesion to the dental amalgam substrate relative to untreated substrates. Alternatively, the oxidant and adhesive may be concurrently applied to the adherend (e.g., dental amalgam, dental alloys or metals).

The term "adherend," as used herein, refers to the surface to which the primer is applied and to which the adhesive adheres. It is presently believed that the primers and adhesives of the present invention will increase adhesion to many typical dental metals, which are capable of being oxidized, including dental alloys and amalgams.

The term "restorative," as used herein, refers to well known dental coating or filling materials such as dental composites, restoratives, glass ionomer cements, sealants, amalgams or other hardenable coatings.

The term "dental amalgam," as used herein, refers to well known conventional dental amalgam alloys. Conventional amalgam preparations are available in capsules which contain amalgam alloy powder and mercury, sealed by a penetrable bladder located at one end of the capsule. The dental clinician prepares an amalgam restorative by first placing the capsule containing the alloy powder and mercury into an amalgamator. The amalgamator, or triturator as it is often called, vibrates at high speed so that the metal rod within the capsule can penetrate the bladder to release the mercury contained therein. As mercury admixes into the alloy powder a reaction occurs between alloy powder and mercury and the amalgam slowly begins to set. At this stage the amalgam is ready for packing into the tooth cavity.

Conventional alloy powders are typically mixtures of silver, tin, copper, and zinc. Conventional amalgam alloy powders have proper proportioning of these metals to result in an alloy described in the art as a "balanced alloy." For example, it is known that increasing the silver content increases the expansion of the setting amalgam, shortens setting time, increases compressive strength, and tends to make the alloy mixture more difficult to amalgamate. Tin behaves in an opposite way for all these properties. Copper and zinc contribute properties similar to silver with respect to expansion, setting time and strength, but copper is used principally for increased strength and zinc for increased resistance to tarnish.

Conventional alloys are broadly classified as low copper alloys (5% or less copper) and high copper alloys (13% to 30% copper). Commercially available low copper amalgam alloys contain typically the following compositions which apply to lathe-cut or spherical particle shapes: silver (63–70%), tin (26–28%), copper (2–5%), and zinc (0–2%). Commercially available high copper alloys using lathe-cut particles contain typically the following compositions: silver (40–70%), tin (26–30%), copper (2–30%), and zinc (0–2%). Commercially available high copper alloys using spherical particles contain typically the following compositions: silver (40–65%), tin (0–30%), copper (20–40%), zinc (0%), and palladium (0–1%). Mercury typically represents 40 to 60 percent by weight of the amalgam mixture. One high copper amalgam alloy is available under the trademark "DISPERSALLOY" alloy from the L.D. Caulk Division, Dentsply International Inc. The "DISPERSALLOY" alloy contains about 13% copper and the mixed "DISPERSALLOY" amalgam contains about 50% mercury.

Amalgams have been the dental restorative of choice for over a century and offer many benefits to the dental clinician such as a relatively simple placement technique, easy adaptation to the tooth cavity, low cost per application, long term retention, and minimal wear of opposing dentition. However, dental amalgams have serious limitations which make them less desirable. For example, conventional dental amalgams lack adhesion to both tooth structure and esthetic composite materials. As a result, restorations employing amalgam materials may exhibit marginal leakage and offer poor esthetics.

As previously discussed, the primary components of dental amalgams include metallic mercury, silver, and tin. It is presently believed that the redox properties of the mixed amalgam alloy are a function of these individual components. Therefore, the ability to oxidize an amalgam may be governed by the formal electrode potential of silver, mercury and fin half reactions as shown below:

$Hg^O \rightarrow Hg^{2+}+2e$ $E^O=-0.854$ Volts $Ag^O \rightarrow Ag^{+}+e$ $E^O=-0.799$ Volts $Sn^O \rightarrow Sn^{2+}+2e$ $E^O=0.136$ Volts The electromotive force of a redox reaction may be calculated by combining half cell potentials as follows: $E^O$ cell=$E^O$ oxidant+$E^O$ reductant. For combinations where the sum of $E^O$ oxidant and $E^O$ reductant is greater than zero a redox reaction is expected to occur. Mercury and silver comprise the greatest proportion of a conventional amalgam composition. For most common dental amalgams, it has been discovered that oxidants with electrode potentials ("$E^O$ oxidant") greater than about 0.8 Volts induce amalgam surface modifications and enhance the adhesion of dental adhesives and composites to the amalgam surface.

The primer of the present invention comprises an oxidant and optionally a solvent. The oxidant can be liquid or a solid; if a solid it should be dissolved or dispersed in a suitable solvent to enable the oxidant to wet the amalgam substrate. Liquid oxidants can also be dissolved in a suitable solvent, e.g., in order to facilitate wetting. More particularly, the oxidant should be sufficiently compatible with the solvent to provide the desired degree of adhesion for the particular amalgam substrate and application involved. For example, on amalgam the degree of adhesion preferably is sufficient to provide an average measured shear strength of at least 7 MPa, more preferably at least 8 MPa, and most preferably at least 10 MPa according to the test method described below.

Suitable oxidants for use in the present invention have electrode oxidation potentials greater than the absolute value of the $E^O$ reductant of the adherend (e.g., the amalgam substrate) and are preferably soluble or dispersible in a suitable solvent and at a sufficient concentration to provide the desired surface modification to the adherend. Preferred oxidants for use in the present invention have electrode oxidation potentials greater than about 0.8 Volts. More preferred oxidants have electrode oxidation potentials between about 0.8 Volts and about 3.0 Volts.

Suitable oxidants for use in the present invention include anionic, cationic or neutral species and mixtures thereof. Suitable anionic oxidants for use in the present invention include acids or salts of the following anions including: $NO_2-$, $NO_3-$, $ClO-$, $ClO_3-$, $ClO_4-$, $BrO-$, $BrO_3-$, $IO-$, $IO_3-$, $MnO_4-$, $Cr_2O_7-$, and $S_2O_8^{-2}$. Suitable cationic oxidants for use in the present invention include salts of the following cationic species including: $Ru^{+4}$, $Cr^{+6}$, $Rh^{+4}$, $Ce^{+4}$, $Mn^{+3}$, $Co^{+3}$, and $Cu^{+2}$. Suitable neutral (non-ionic) oxidants for use in the present invention include: $ClO_2$, $Br_2$, $MnO_2$, and $H_2O_2$.

Preferred oxidants for use in the present invention include: $NO_3-$, $MnO_4-$, $Cr_2O_7-$, $S_2O_8^{-2}$, and $H_2O_2$.

The oxidants of the present invention are preferably combined with one or more solvents and applied to the amalgam surface in the form of a primer solution. The solvent(s) aid in wetting the amalgam substrate and in solubilizing or dispersing the oxidant. The solvent also assists in the transport of electrons and thereby facilitates the oxidation reaction. Suitable solvents for the oxidants of the present invention are organic solvents (including water) which are capable of dissolving or suspending the oxidant. As previously mentioned, the oxidant may alternatively be dissolved or suspended in the adhesive. In that case the adhesive may serve to act as the solvent or as a cosolvent to the oxidant.

Preferred solvents for the oxidants of the present invention are polar solvents. By "polar solvent" is meant a solvent which comprises polar molecules which ionize in solution and impart electrical conductivity. An important property of polar solvents to be considered is the dielectric constant, "$\epsilon$". The dielectric constant gives a rough guide to solvent properties. For example, the dielectric constant of a substance measures the reduction of the strength of the electric field surrounding a charged particle immersed in the substance, compared to the field strength around the same particle in a vacuum. In general, and for purposes of this invention, polar solvents have a dielectric constant greater than or equal to about 15 ($\epsilon \geq \sim 15$), while nonpolar solvents have a dielectric constant less than about 15 ($\epsilon < \sim 15$). Preferred solvents for use in this invention have a dielectric constant greater than or equal to about 15. More preferred solvents for use in this invention have a dielectric constant greater than about 30. Most preferred solvents for use in this invention have a dielectric constant greater than about 70.

Suitable solvents include, for example, water, alcohols such as methanol, ethanol, 1-propanol, 2-propanol, and 2-methyl-2-propanol, ketones such as acetone and methylethylketone, aldehydes such as formaldehyde, acetaldehyde, propionaldehyde, acrolein, glutaraldehyde and 2-hydroxy-adipaldehyde, amides such as acetamide and N,N-dimethylformamide, and other substances such as tetrahydrofuran and dimethyl sulfoxide. Water is most preferred. The primer preferably contains less than about 95 weight percent solvent, more preferably between about 20 and about 95 weight percent solvent, most preferably between about 30 and about 95 weight percent solvent.

A suitable amount of oxidant to be dissolved in the solvent will be between about 0.001 Molar ("M") and the limit of solubility. More preferably, the amount of oxidant to be dissolved in the solvent will be between about 0.1M and about 15M. Most preferably, the amount of oxidant to be dissolved in the solvent will be between about 1M and about 12M. The optimum amount depends in part on the $E^O$ oxidant value for the particular oxidant. For example, for nitric acid, concentrations between about 0.8M and about 15M are preferred.

The oxidant and optional solvent should be allowed to stand on the surface of the substrate long enough to provide the desired degree of priming. The standing time will depend upon the particular oxidant and adhesive employed, the type of substrate and its intended use, and the time available for carrying out the priming procedure. For priming amalgam, standing times less than about 5 minutes, and preferably about 5 seconds to one minute provide very effective priming, although shorter or longer times can be used if desired.

Suitable adhesive compounds (hereinafter referred to as the "adhesive" or the "compound") for use in the present invention include compositions which have been found to have utility in bonding dental composites to hard tissue such as dentin, enamel, bone, or the like. Typically, such adhesives comprise organic monomers, oligomers, polymers, or cosolvents, and are capable of forming a hardenable (e.g., polymerizable) continuous or semicontinuous film on the surface of the adherend. In addition, such adhesives typically have a relatively low viscosity, i.e., are flowable, prior to being crosslinked or polymerized. The adhesive, prior to removal of any volatile components, preferably wets the adherend and most preferably has a sufficiently low viscosity to enable it to flow into interstices that already exist in the surface of the adherend or that are created therein by the action of the oxidant. After removal of any volatile components the adhesive preferably has a sufficiently high viscosity to enable it to resist displacement by dentinal fluids or other extraneous liquids. Preferably the adhesive is suitable for use in the oral environment both in its unpolymerized and polymerized state. Both phosphorylated and phosphorus-free ethylenically unsaturated compounds as well as mixtures thereof are suitable. Water-based cements such as glass ionomer cements, as discussed below, are also suitable as the adhesive composition.

If desired, two or more applications of adhesive may be employed. For example, a first adhesive composition may be applied to the primed adherend, followed by the application of a second adhesive composition of either the same or a different adhesive. It is preferable that the first adhesive composition be compatible with the optional second adhesive composition (e.g., the first adhesive composition be either capable of forming a homogeneous solution when combined with the second adhesive composition, capable of copolymerizing or crosslinking with the second composition, or both). Additionally, the first adhesive composition may optionally be hardened prior to the application of the optional second adhesive composition.

To assist in hardening, the adhesive preferably contains one or more crosslinkable substances or polymerizable substances. Addition polymerizable substances (e.g., vinyl compounds such as acrylates and methacrylates) are especially preferred. The adhesive can also contain appropriate polymerization catalysts (e.g., photoinitiators) to assist in hardening the adhesive.

Suitable phosphorus-free ethylenically unsaturated compounds for use in the adhesive include mono- or poly- (e.g., di-, tri- or tetra-functional) acrylates and methacrylates such as methyl acrylate, 2-hydroxyethyl acrylate, 2-hydroxyethylmethacrylate ("HEMA"), triethyleneglycol diacrylate, triethyleneglycol dimethacrylate, polyethyleneglycol (400) diacrylate and dimethacrylate, neopentylglycol diacrylate, hexamethyleneglycol diacrylate, trimethylolpropane triacrylate, pentaerythritol tetraacrylate, polyalkylene glycol mono- and di-acrylates, urethane mono- or poly-functional acrylates, 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl- 1,2-diacrylate and dimethylacrylate, pentaerythritol diacrylate and dimethacrylate, pentaerylthritol trimethacrylate and triacrylate, acrylic acid, methacrylic acid, 2-trimethylammonium ethylmethacrylic chloride, glycerol dimethacrylate and diacrylate, gylcerol monomethacrylate and monoacrylate, Bisphenol A diacrylates, tetrahydrofurfural methacrylate, glyceryl- 1,3-dimethacrylate, ethyl methacrylate, n-hexyl methacrylate, and 1,6-hexanediol dimethacrylate, and the corresponding acrylates or methacrylates of the above compounds, as well as acrylamides and methacrylamides such as 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, methacrylamidopropyltrimethylammonium chloride, N-alkyl-N-hydroxyethyl acrylamides and methacrylamides, 2- and 3-hydroxypropylacrylamide and methacrylamide, vinyl compounds, styrene compounds, and other olefinically unsaturated compounds suitable for use in the oral environment and mixtures thereof. U.S. Pat. Nos. 4,499,251, 4,515,930, 4,537,940 and 4,539,382 contain an extensive list of such compounds. A particularly preferred adhesive is obtained by combining the dimethacrylate derived from the reaction between methacrylic acid and the diglycidyl ether of bisphenol A ("Bis-GMA") with a hydrophilic monomer such as HEMA, hydroxypropyl methacrylate, or methacrylic acid.

Representative phosphorus-free ethylenically unsaturated dental adhesives include "SCOTCHBOND 2™" Dental Adhesive (3M), "SCOTCHBOND™" Multi-Purpose Dental Adhesive (3M), "CONCISE™" Enamel Bond (3M), "TENURE™" Solution Dentin Bonding System (Den-Mat Corp.), "GLUMA™" Bonding System (Columbus Dental Miles, Inc.) and "MIRAGE-BOND™" Dentin-Enamel Bonding System (Chameleon Dental Products, Inc.), see U.S. Pat. Nos. 4,514,527, 4,521,550, 4,588,756, and 4,659,751.

Suitable polymer components for use in the adhesive include linear, branched or cyclic polymers formed prior to the hardening step. For purposes of this invention, a polymer is a chemical compound having at least two repeat units. They can be polymers of ethylenically unsaturated monomers or they can be polymeric compounds like polyester, polyamide, polyether, polyethyleneglycol, polyethyleneglycol dimethacrylate and diacrylate, polysaccharide, cellulosic, polypropylene, polyacrylonitrile, polyurethane, poly(vinyl chloride), poly(methyl methacrylate), phenol-formaldehyde, melamine-formaldehyde, and urea-formaldehyde. Mixtures of such polymers can be used if desired.

Preferred polymers are the polymers of ethylenically unsaturated monomers. These polymers may be homo- or co-polymers and may contain hydrophilic or hydrophobic groups. The polymer may optionally contain acid groups, their salts, or their reactive derivative groups. Particularly preferred polymers contain reactive groups that further react (i.e., crosslink or copolymerize) with the other components of the adhesive, or the dental restorative. Addition polymerizable reactive groups (e.g., vinyl groups such as acrylates and methacrylates) are especially preferred.

Polymers of ethylenically unsaturated monomers are often used in dental glass ionomer cements. These polymers are especially useful in the present invention as they generally have good biocompatibility and have a suitable molecular weight. The polymer component of an ionomer cement is often a copolymer of acrylic acid and itaconic acid, although other monomers may be incorporated, and are herein referred to as polyalkenoic acids. See generally, Prosser et al., *Developments in Ionic Polymers*-1, Chapter 5, Applied Science Publishers (London and New York, 1983). Recently such polymers have been further modified in the laboratory of the assignee of this invention by the incorporation of addition polymerizable reactive groups as mentioned above. Their preparation is described below and in U.S. Pat. No. 5,130,347.

Suitable polymeric compounds of the invention have a weight average molecular weight prior to hardening of more than about 1000, although preferably no greater than 2,000,000. More preferably, polymeric compounds of the invention have a weight average molecular weight prior to hardening of between about 1,000 and 1,000,000 evaluated against a polystyrene standard using gel permeation chromatography. Most preferably, polymeric compounds of the invention have a weight average molecular weight prior to hardening of between about 5,000 and 200,000.

Suitable ethylenically unsaturated phosphorylated compounds comprise one or more phosphorus atoms bonded through a carbon, nitrogen, oxygen, or sulfur atom to a radical containing one or more ethylenically unsaturated groups. Preferred ethylenically unsaturated groups are ethenyl and 2-propenyl as found, respectively, in acrylate and methacrylate groups. One or more of the phosphorus atoms can be bonded to one or more halogen atoms, active hydrogen atoms, or substituted or unsubstituted hydrocarbyl groups (e.g., an alkyl, aryl, alkaryl, or aryalkyl group). A particular class of suitable phosphorylated compounds is described in European Patent Application No. 0 058 483 and U.S. Pat. No. 4,515,930. These phosphorylated compounds include those comprising an organic ester of one or more acids of phosphorus, the organic radical of said ester containing at least one ethylenically unsaturated group, wherein said ester has chlorine or bromine bonded directly to the phosphorus (hereinafter "halophosphorus acid esters"). A preferred subclass of such halophosphorus acid esters includes halophosphorus acid esters of diglycidyl methacrylate of Bisphenol A ("Bis-GMA") prepared by reacting Bis-GMA with a phosphorus acid halide. Phosphorus acid halides (e.g., chlorides, bromides) that can be reacted with Bis-GMA include $POCl_3$, $PCl_3$, $PBr_3$, $R'OP(O)Cl_2$, $(R'O)_2P(O)Cl$ where R' is a hydrocarbyl radical, preferably one derived from removal of one or more hydroxyl groups from a hydroxyl-containing compound such as 2-hydroxyethyl methacrylate, ethylene glycol, polyethylene glycol, pentaerythritol, and the like, as would result from a reaction of the hydroxyl-containing compound and the phosphorus acid halide. A particularly preferred class of phosphorylated compounds includes chlorophosphorus acid esters of Bis-GMA.

An additional suitable class of phosphorylated compounds includes the phosphorus acid esters described in U.S. Pat. Nos. 3,882,600, 3,997,504, 4,222,780, 4,235,633, 4,259,075, 4,259,117, 4,368,043, 4,442,239, 4,499,251, 4,514,342, 4,537,940, 4,539,382, 4,657,941, 4,816,495, 4,966,934 and Japanese published patent application (Koho) No. 85-17235. Exemplary members of this class are the compounds 2-methacryloyloxyethyl phenyl phosphate and 10-methacryloyloxydecyl dihydrogen phosphate.

A further suitable class of phosphorylated compounds includes the pyrophosphate ester derivatives described in U.S. Pat. Nos. 4,383,052 and 4,404,150 and in Japanese Kokai 57-143372 and 57-167364. Glycerophosphate dimethacrylate is also suitable.

The adhesive preferably comprises one or more suitable cosolvents. The cosolvent(s) aid in wetting the adherend and in solubilizing or dispersing the adhesive substances. Suitable cosolvents include water, alcohols such as methanol, ethanol, 1-propanol, 2-propanol, and 2-methyl-2-propanol, ketones such as acetone and methylethylketone, aldehydes such as formaldehyde, acetaldehyde, propionaldehyde, acrolein, glutaraldehyde and 2-hydroxy-adipaldehyde, amides such as acetamide and N,N-1 5 dimethylformamide, and other substances such as tetrahydrofuran and dimethyl sulfoxide. The adhesive preferably contains less than about 95 weight percent cosolvent, more preferably less than about 85 weight percent cosolvent, most preferably less than about 50 weight percent cosolvent.

Other adjuvants such as polymerization catalysts, medicaments, fluoride compounds, indicators, dyes, wetting agents, buffering agents, fillers, thixotropes and the like can be included in the adhesive, contingent upon attainment of the desired degree of bonding performance and suitability for use on the desired adherend.

It is also worth noting that a number of water-based cements used in dentistry are useful in the present invention. These water-based cements may contain some of the same ingredients as the aforementioned adhesives, but are distinguished from the adhesives by having a much higher viscosity and recommended use in load bearing application. Furthermore, these cements employ reactive glass fillers which assist in the crosslinking of the composition. Examples include metal oxide cements such as those described in U.S. Pat. No. 3,655,605 and fluoroaluminosilicate glass cements (also known as "glass ionomer cements") such as those described in Example 6 of the '605 patent and in U.S. Pat. Nos. 3,814,717, 4,043,327, 4,143,018, 4,209, 434, 4,872,936, and 5,130,347; European Pat. Application No. 0 329 268; and Australian Published Pat. Specification No. 46717/89.

Generally, when a water-based cement is used as the adhesive it is formulated in two parts, although formulations employing three or more parts can be made up if desired. In a two part formulation, the first part typically is a powder portion containing the acid-reactive filler. The second part typically is a liquid portion containing an acidic polymer and water. The water-based cement may optionally contain monomers of the type listed above.

The invention is not limited to powder:liquid formulations. For example, one part anhydrous formulations containing filler, polymer, reducing agent and oxidizing agent can be prepared. These can be sold in dry form and prepared for use by adding water. Also, two part paste:paste formulations can be prepared by adding to the acid-reactive filler a suitable polymerizable liquid that does not react with that filler (e.g., 2-hydroxyethyl methacrylate, or "HEMA"), yielding a first paste. The acidic polymer described above is combined with a suitable filler that does not react with the acidic polymer (e.g., ground quartz), yielding a second paste. The two pastes are prepared for use by admixing them. The combined pastes preferably have a sufficiently low filler loading and sufficiently low viscosity so that their mixture will be useful as a dental adhesive. Other useful configurations will be familiar to those skilled in the art. However, for simplicity, the remainder of this patent specification will refer to powder:liquid formulations unless specifically noted otherwise.

The adhesive may contain water. The water can be present in the product as sold, or added by the dentist just prior to use. The water can be distilled, deionized or plain tap water. Generally, deionized water is preferred. The amount of water should be sufficient to provide adequate handling and mixing properties and to permit the transport of ions in the filler-acid reaction. Preferably, water represents at least about 1%, more preferably about 3% to about 60%, and most preferably about 5% to about 40% of the total weight of ingredients used to form the adhesive.

In general, water-based cements are ionically hardenable. By this is meant that they contain ingredients that, when combined, can react via an ionic reaction to produce a hardened mass. The ionic reaction occurs between acid groups on the polymer and acid-reactive groups on the filler.

Preferably, the water-based cement also contains ethylenically-unsaturated groups. In other words, they preferably contain at least one ethylenically-unsaturated moiety. The ethylenically-unsaturated moiety can be present as a separate ingredient (for example, as an acrylate- or methacrylate-functional monomer) or it can, if desired, be present as a group on another ingredient such as the acidic polymer. A wide variety of ethylenically-unsaturated moieties can be used. A useful list of suitable materials is shown at page 9, line 13 through page 13, last line of Australian Published Pat. Specification No. 46717/89. Of the many materials mentioned, water-miscible or water-soluble acrylates and methacrylates such as 2-hydroxyethyl methacrylate, hydroxymethyl methacrylate, 2-hydroxypropyl methacrylate, tetrahydrofurfuryl methacrylate, glycerol mono- or di- methacrylate, trimethylol propane trimethacrylate, ethylene glycol dimethacrylate, polyethylene glycol dimethacrylate, urethane methacrylates, acrylamide, methacrylamide, methylene bis-acrylamide or methacrylamide, and diacetone acrylamide and methacrylamide are preferred. Mixtures of ethylenically-unsaturated moieties can be used if desired. Preferably, the ethylenically-unsaturated moieties are present as groups on the acidic polymer, as described in more detail below. The ethylenically-unsaturated groups are preferably capable of free radical polymerization or crosslinking when promoted by a suitable catalyst (e.g., a photoinitiator and/or a reducing agent: oxidizing agent combination).

In general, the water-based adhesive contains an acid-reactive filler. The filler should be sufficiently finely-divided so that it can be conveniently mixed with the other adhesive ingredients and used in the mouth. Preferred average particle diameters for the filler in the cement is about 0.2 to about 15 micrometers, more preferably about 1 to 10 micrometers, as measured using, for example, a sedimentation analyzer. Suitable acid-reactive fillers include metal oxides, metal salts and glasses. Preferred metal oxides include barium oxide, calcium oxide, magnesium oxide and zinc oxide. Preferred metal salts include salts of multivalent cations, for example aluminum acetate, aluminum chloride, calcium chloride, magnesium chloride, zinc chloride, aluminum nitrate, barium nitrate, calcium nitrate, magnesium nitrate, strontium nitrate and calcium fluoroborate. Preferred glasses include borate glasses, phosphate glasses and fluoroaluminosilicate glasses. Fluoroaluminosilicate glasses are particularly preferred. Suitable fillers are also available from a variety of commercial sources familiar to those skilled in the art. For example, suitable fillers can be obtained from a number of commercially available glass ionomer cements, such as "GC Fuji LC™" adhesive and "Kerr XR™" ionomer cement. Mixtures of fillers can be used if desired.

If desired, the filler can be subjected to a surface treatment. Suitable surface treatments include acid washing, treatment with phosphates, treatment with chelating agents such as tartaric acid, treatment with a silane as described in Australian Published Pat. No. 46717/89, and treatment with a silanol solution.

The amount of filler should be sufficient to provide an adhesive having desirable mixing and handling properties before hardening, and good adhesive performance after hardening. The filler preferably represents less than about 90%, more preferably about 25% to about 85%, and most preferably about 30% to about 75% by weight of the total weight (including water) of the unhardened adhesive components.

The acidic polymer need not be entirely water-soluble, but it should be at least sufficiently water-miscible so that it does not undergo substantial separation when combined with the liquid ingredients of the adhesives. Suitable acidic polymers include those listed at column 2, line 62 through column 3, line 6 of U.S. Pat. No. 4,209,434, which is herein incorporated by reference. Preferred acidic polymers include homopolymers and copolymers of alkenoic acids such as acrylic acid, itaconic acid and maleic acid. Suitable polymers are also available from a wide variety of commercial sources, and many are found in currently-available glass ionomer cements. As will be appreciated by those skilled in the art, the polymer should have a molecular weight sufficient to provide good storage, handling and mixing properties. A preferred molecular weight is about 2000 to about 100,000 weight average molecular weight ("Mw"), evaluated against a polystyrene standard using gel permeation chromatography. The acidic polymer preferably contains one or more ethylenically-unsaturated groups. Suitable ethylenically-unsaturated acidic polymers are described in U.S. Pat. Nos. 4,872,936 and 5,130,347. Preferably, the numbers of acid groups and ethylenically-unsaturated groups are adjusted to provide an appropriate balance of properties in each adhesive, both during the setting reaction and after the adhesive has hardened. Acidic polymers in which about 10 to about 30% of the acidic groups have been replaced with ethylenically-unsaturated groups are preferred.

The amount of acidic polymer in each adhesive should also be sufficient to provide a desired balance of physical properties. A preferred acidic polymer amount is at least about 5%, more preferably about 10 to about 50%, and most preferably about 10 to about 30% of the total weight (including water) of the unhardened adhesive components.

Polymerization catalysts that can be included in the adhesive are autocure or light cure catalysts (i.e., catalysts which are sensitive to actinic radiation such as visible light) such as those mentioned in columns 28 and 29 of U.S. Pat. No. 4,539,382, chromophore-substituted halomethyl-s-triazines such as those shown in U.S. Pat. No. 3,954,475, chromophore-substituted halomethyl-oxadiozoles such as those shown in U.S. Pat. No. 4,212,970, and aryliodonium salts such as those shown in European Patent Application 0 290 133.

The optional photoinitiator of the adhesives of the present invention should be capable of promoting free radical crosslinking of the ethylenically-unsaturated component on exposure to light of a suitable wavelength and intensity. It also preferably is sufficiently shelf-stable and free of undesirable coloration to permit its storage and use under typical dental conditions. Visible light photoinitiators are preferred. For water-based adhesives, the photoinitiator preferably is water-soluble or water-miscible. Photoinitiators bearing polar groups usually have a sufficient degree of water-solubility or water-miscibility. The photoinitiator frequently can be used alone but typically it is used in combination with a suitable donor compound or a suitable accelerator (for example, amines, peroxides, phosphorus compounds, ketones and alpha-diketone compounds).

Preferred visible light-induced initiators include camphorquinone ("CPQ", which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate ("DPIHFP"), with or without additional hydrogen donors (such as sodium benzene sulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the adhesive layer to be exposed to radiant energy, and the extinction coefficient of the photoinitiator. Typically, the photoinitiator components will be present at a total weight of about 0.01 to about 5%, more preferably from about 0.1 to about 5%, based on the total weight (including optional water) of the unhardened adhesive components. For water-based cement adhesives, the photoinitiator can be included in either the powder or liquid parts of each adhesive.

A preferred initiator system for use in water-based cements which contain ethylenically-unsaturated groups is a combination of a water-soluble reducing agent and a water-soluble oxidizing agent. The water-soluble reducing agent and water-soluble oxidizing agent are most conveniently discussed together. They should react with or otherwise cooperate with one another to produce free radicals capable of initiating polymerization of the ethylenically-unsaturated moiety. The reducing agent and oxidizing agent preferably are sufficiently shelf-stable and free of undesirable colorization to permit their storage and use under typical dental conditions. They should be sufficiently water-soluble to permit ready dissolution in (and discourage separation from) the other components. Preferably, the reducing agent and oxidizing agent should be sufficiently soluble that at least 200 parts per million may be readily dissolved in water, and no undissolved material will be observed after the solution has remained undisturbed for one week. The reducing agent and oxidizing agent should also be sufficiently soluble and present in an amount sufficient to permit an adequate free radical reaction rate. This can be evaluated by combining all of the ingredients of the adhesive, except for the filler, under safelight conditions, and observing whether or not a hardened mass is obtained. The reducing agent and oxidizing agent preferably are sufficiently water-soluble and have sufficient reduction and oxidation potentials to initiate gelation of an aqueous crosslinkable acrylamide solution. This can be evaluated by adding 2 weight % each of the reducing agent and the oxidizing agent to an aqueous acrylamide methylene bis-acrylamide solution (described in Table Ia of U.S. Pat. No. 5,154,762, which patent is herein incorporated by reference) and observing whether or not gelation occurs within 30 minutes. Useful reducing agent/ oxidizing agent pairs are shown in "Redox Polymerization," G. S. Misra and U. D. N. Bajpai, *Prog. Polym. Sci.*, 8, 61–131 (1982).

Preferred reducing agents include ascorbic acid, cobalt (II) chloride, ferrous chloride, ferrous sulfate, hydrazine, hydroxylamine (depending upon the choice of oxidizing agent) oxalic acid, thiourea, and salts of a dithionite or sulfite anion. Preferred oxidizing agents include cobalt (III) chloride, tert-butyl hydroperoxide, ferric chloride, hydroxylamine (depending upon the choice of reducing agent), perboric acid and its salts, and salts of a permanganate or persulfate anion. Hydrogen peroxide can also be used, although it may interfere with the optional photoinitiator if the latter is present.

The amount of reducing agent and oxidizing agent should be sufficient to provide the desired degree of polymerization of the ethylenically-unsaturated component. The preferred amount for each of the reducing agent and oxidizing agent is about 0.01 to about 10%, more preferably about 0.02 to about 5%, based on the total weight (including water) of the adhesive components.

The reducing agent or the oxidizing agent can be microencapsulated. This will generally enhance shelf stability and permit packaging both the reducing agent and oxidizing agent together. For example, through appropriate selection of the encapsulant, both the oxidizing agent and reducing agent can be combined with the filler and kept in a storage-stable state. Likewise, through appropriate selection of a water-insoluble encapsulant, the reducing agent and oxidizing agent can be combined with water and the acidic polymer and maintained in a storage-stable state.

Either water-soluble or water-insoluble encapsulants can be employed. However, water-insoluble encapsulants are preferred, as they generally provide better long term storage stability under moist or humid conditions. Although the use of a water-insoluble encapsulant may initially seem inappropriate in a water-based adhesive, it has been found that vigorous mechanical mixing generally will be sufficient to break apart the capsule walls and permit adequate release of the encapsulated reducing agent or oxidizing agent and subsequent hardening or cure of the adhesive.

Preferably the encapsulant is a medically acceptable polymer. Also, the glass transition temperature (Tg) of the encapsulant preferably is above room temperature.

A wide variety of encapsulants can be used, with cellulosic materials such as cellulose acetate, cellulose acetate butyrate, ethyl cellulose, hydroxymethyl cellulose and hydroxyethyl cellulose being preferred. Other encapsulants include polystyrene, copolymers of polystyrene with other vinylic monomers, polymethylmethacrylate, copolymers of methylmethacrylate with other ethylenically-unsaturated monomers, and other materials that will be familiar to those skilled in the art of encapsulation.

The capsules themselves need not be perfectly spherical nor uniformly shaped. It is merely sufficient that they entrain or entrap the encapsulated reducing agent or oxidizing agent in a manner sufficient to permit storage of the encapsulated material in the adhesive without leading to undesirable premature polymerization.

To encapsulate the reducing agent or oxidizing agent in a water-insoluble encapsulant, it is preferred to dissolve the encapsulant in a suitable water-immiscible solvent such as methyl acetate, ethyl acetate or methylene chloride. Meanwhile, the reducing agent or oxidizing agent is dissolved in water. The water solution can then be added to the solution of encapsulant and water-immiscible solvent. Stirring or other high speed shear techniques preferably are used to promote uniform microcapsule formation. The capsule shells are formed around the aqueous solution droplets either by evaporation of the water-immiscible solvent or by the addition of a second water-immiscible solvent (e.g., n-hexane) that will precipitate the encapsulant. The capsules can then be removed by cooling and filtration.

To encapsulate the reducing agent or oxidizing agent in a water-soluble encapsulant, the dry reducing agent or oxidizing agent is preferably suspended in a stirred solution of the encapsulant in a water-immiscible organic solvent. Vigorous stirring will promote uniform encapsulation of the reducing agent or oxidizing agent. The capsules can be formed by evaporation or by precipitation and then removed using the techniques described above.

The adhesive can optionally contain a chelating agent. Preferred chelating agents include tartaric acid, ethylene diamine tetraacetic acid, citric acid, the salts of these acids, and the like.

As also mentioned above, the primer and adhesive preferably are overcoated with a conventional restorative or coating. The hard tissue can then be finished using conventional techniques. For example, on tooth tissue, the primer can be overcoated with a dental adhesive, dental ionomer cement and/or a dental restorative and used, for example, to restore teeth, to install crowns, bridgework or other prosthetic devices, or to bond orthodontic brackets to the adherend.

The primers, adhesives and restoratives of the present invention are preferably packaged in "kits" containing the materials and any optional applicator devices such as brushes, droppers, spatulas or sponges. More preferably, the kits also include an amalgam material.

Shear Strength Test Method

Adhesion of composite restorative to previously set amalgam was evaluated as follows. Acrylic cylinders of 25 mm diameter and 10 mm height were prepared, and a hole of 6 mm diameter by approximately 3 mm depth was drilled into the center of each acrylic cylinder. DISPERSALLOY™ amalgam was triturated per manufacturer's directions and transferred into the holes within the acrylic cylinders. The amalgam samples were then allowed to set for 15 minutes, transferred to water and stored at 37° C. for at least 24 hours. The exposed portion of each amalgam was ground flat and parallel to the acrylic cylinder using 120 silica carbide paper-backed abrasive on a lapidary wheel in order to expose the amalgam surface. During this and subsequent grinding and polishing steps, the amalgam samples were continuously rinsed with water. Further polishing was carried out by mounting grade 600 paper-backed abrasive on the lapidary wheel. The amalgam samples were stored in water and used within 2 hours after polishing. The polished amalgams were removed from the water and dried using a stream of compressed air prior to use.

A primer solution of one of the oxidants of this invention was applied to the amalgam surface, allowed to stand for 30 seconds, rinsed with water and dried with oil free air. At least one layer of adhesive composition was then applied onto the dry surface and cured as appropriate. A previously prepared mold made from 2.5 mm thick "teflon" sheet with a 5 mm diameter hole through the sheet was fitted with a gelatin capsule sleeve, yielding a 4.72 mm diameter hole, and clamped to the primed amalgam sample. The hole was filled with a visible light-cure dental restorative (e.g., P-5™ Universal shade, available from 3M) and cured using a 30 second irradiation from a VISILUX™ 2 curing light (available from 3M). The sample and mold were allowed to stand for 5 minutes at room temperature and were then stored in distilled water at 37° C. for 24 hours. The mold was then carefully removed from the sample leaving a button-like molded plug of restorative attached to the sample surface.

Adhesive strength was evaluated by mounting the acrylic disk in a holder clamped in the jaws of an "Instron" apparatus, with the polished sample surface oriented parallel to the direction of pull. A loop of wire (0.4 mm diameter) was placed around the restorative button adjacent to the polished sample surface. The ends of the wire were clamped in the pulling jaws of the Instron apparatus, thereby placing the bond in shear stress, and pulled at a crosshead speed of 2 mm/min until failure occurred.

The following examples are offered to aid in the understanding of the present invention and are not to be construed as limiting the scope thereof. Unless otherwise indicated, all parts and percentages are by weight.

PREPARATORY EXAMPLE 1

Preparation of Tricure Ionomer Composition

A "tricure" ionomer composition was prepared by mixing a powder and a liquid as described below. The liquid was prepared by mixing the ingredients set out below in Table A.

TABLE A

| Ingredients | (parts) |
| --- | --- |
| VBP[1] | 50 |
| Water | 30 |
| HEMA | 20 |
| DPIHFP | 1.0 |
| CPQ | 0.25 |
| BHT[2] | 0.10 |

[1]("VBP") = the precipitated dry polymer of EXAMPLE 11 of U.S. Pat. No. 5,130,347.
[2]("BHT") = butylated hydroxytoluene (also known as 2,6-Di-tert-butyl-4-methylphenol).

The powder contained a glass and two separate granular microcapsules. The glass was prepared by first mixing the ingredients set out below in Table B. The ingredients were next melted in an arc furnace at about 1350°–1450° C., poured from the furnace in a thin stream and quenched using chill rollers to provide an amorphous single-phase fluoroaluminosilicate glass.

TABLE B

| Ingredient | Amount |
| --- | --- |
| $SiO_2$ | 37 |
| $AlF_3$ | 23 |
| SrO | 20 |
| $Al_2O_3$ | 10 |
| $AlPO_4$ | 7 |
| $Na_3AlF_6$ | 6 |
| $P_2O_5$ | 4 |

The glass was ball-milled to provide a pulverized frit with a surface area of 3.0 $m^2/g$ measured using the Brunauer, Emmet and Teller ("BET") method. Four parts "A-174" gamma-methacryloxypropyl trimethoxysilane (Union Carbide Corp.), 0.44 parts glacial acetic acid, 25 parts methanol, and 25 parts water were mixed for 15 minutes at room temperature, yielding a silanol-containing solution. One hundred parts of the above prepared glass were combined with the silanol treating solution, slurried for 1.5 hours at room temperature, dried overnight at 45° C., and sieved through a 74 μm mesh screen.

Granular ascorbic-acid containing spherical microcapsules were formed by mixing 2.38 parts ascorbic acid in 47.62 parts water with 366 parts of a 1% solution of cellulose acetate butyrate in ethyl acetate. The mixture was maintained at 4° C. by immersing the vessel in a ice-water bath and stirred at 700 rpm. 267 Parts of ice cold n-hexane were added to the solution over a thirty minute period. The granular precipitate was filtered, washed with ice cold n-hexane, dried under vacuum and then deagglomerated in an electric mill. Similarly, potassium persulfate containing spherical microcapsules were prepared by substituting $K_2S_2O_8$ for ascorbic acid.

Tricure powder was prepared by milling together for one hour 100 parts silanol treated glass, 0.55 parts ascorbic acid microcapsules, and 0.1 parts $K_2S_2O_8$ microcapsules.

PREPARATORY EXAMPLE 2

Preparation of a Dental Adhesive System

A dental "primer" was prepared by mixing the following ingredients set out below in Table C.

TABLE C

| Ingredients | (parts) |
| --- | --- |
| VBP | 13.3 |
| Water | 46.9 |
| HEMA | 39.8 |

A dental "adhesive" was prepared by mixing the following ingredients set out below in Table D.

Table D

| Ingredients | (parts) |
| --- | --- |
| BisGMA | 61.9 |
| HEMA | 37.1 |
| DPIHFP | 0.25 |
| CPQ | 0.25 |
| EDMAB[1] | 0.50 |

[1]("EDMAB") = ethyl 2-dimethylaminobenzoate (available from Aldrich Chemical Co.).

EXAMPLE 1

Using the shear strength test method previously described, the shear strength of the bond between a dental composite (P-50™, available from 3M) and set amalgam (DISPERSALLOY™) was evaluated. First, the amalgam surfaces were primed with one of the oxidant solutions listed in Table 1. After priming, the surfaces were rinsed with water and dried with a stream of air. The surfaces were then coated with a light cured ionomer cement (tricure ionomer having a 1.4:1 powder to liquid ratio) and irradiated for 40 seconds using a VISILUX™ 2 dental curing lamp (3M). Next, a coating of a light cured dental adhesive (SCOTCHBOND™ Dual Cure adhesive, available from 3M) was applied to the coated surface and cured for 10 seconds using the VISILUX™ 2 lamp. Finally, P-50™ composite (3M) was applied and cured as previously described. Set out in Table 1 are the run #, primer solution, $E^O$ of the oxidant (in Volts), and the mean shear adhesion value (in MPa). Ten samples were tested for each run.

The results show that nearly all samples pretreated with oxidants having half-cell oxidation potentials ($E^O$) greater than 0.8 volts exhibit improved adhesion relative to the untreated control. No enhancement was observed for samples treated with oxidants having half-cell oxidation potentials ($E^O$) less than 0.8 volts.

TABLE 1

| Run # | Primer solution (concentration in water) | $E^O$ (Volts) | Shear adhesive strength, (MPa) |
|---|---|---|---|
| 1 | Ammonium Nitrate (5%) | 0.94 | 10.2 |
| 2 | Hydrogen Peroxide (10%) | 1.77 | 9.0 |
| 3 | Potassium Permanganate (5%) | 1.70 | 8.8 |
| 4 | Nitric Acid (5%) | 0.94 | 8.4 |
| 5 | Potassium Persulfate (4%) | 2.01 | 7.7 |
| 6 | Perchloric Acid (10%) | 1.47 | 7.2 |
| 7 | Cobalt (II) Chloride (5%) | -0.28 | 7.2 |
| 8 | Iron (III) Chloride (5%) | 0.77 | 7.1 |
| 9 | None[1] | | 6.9 |
| 10 | Iron (II) Chloride (2%) | -0.44 | 6.7 |
| 11 | Sulfuric Acid (10%) | 0.17 | 6.7 |

[1]The tricure ionomer and the light cured dental adhesive were applied directly to the polished amalgam surface.

EXAMPLE 2

Amalgam surfaces were pretreated with either a 37% phosphoric acid solution in water or a 30% hydrogen peroxide solution in water. Additional amalgam surfaces were left untreated for comparison. Tricure ionomer adhesives were separately applied to the treated or untreated surfaces in three powder:liquid ratios (0.7:1, 1:1, and 1.4:1) as described in EXAMPLE 1. SCOTCHBOND™ Dual Cure adhesive and P-50™ composite were then sequentially applied to the ionomer surfaces as described in EXAMPLE 1. Set out in Table 2 are the run #, primer solution, $E^O$ of the oxidant (in Volts), the powder:liquid ratio of the tricure composition, and the mean shear adhesion value (in MPa). Five samples were tested for each run.

The results show that a hydrogen peroxide pretreatment ($E^O$ greater than 0.8 Volts) provides a large adhesion enhancement relative to the untreated amalgam, while a phosphoric acid pretreatment ($E^O$ less than 0.8 Volts) has minimal effect on adhesion performance.

TABLE 2

| Run # | Primer solution (concentration in water) | $E^O$ (Volts) | Powder: Liquid Ratio | Shear adhesive strength,[1] (MPa) |
|---|---|---|---|---|
| 1 | None | | 0.7:1 | 7.6 |
| 2 | Phosphoric Acid (37%) | -0.28 | 0.7:1 | 5.7 |
| 3 | Hydrogen Peroxide (30%) | 1.77 | 0.7:1 | 10.6 |
| 4 | None | | 1:1 | 6.1 |
| 5 | Phosphoric Acid (37%) | -0.28 | 1:1 | 5.9 |
| 6 | Hydrogen Peroxide (30%) | 1.77 | 1:1 | 14.5 |
| 7 | None | | 1.4:1 | 6.1 |
| 8 | Phosphoric Acid (37%) | -0.28 | 1.4:1 | 8.0 |
| 9 | Hydrogen Peroxide (30%) | 1.77 | 1.4:1 | 15.4 |

[1]Mean of 5 samples.

EXAMPLE 3

Amalgam surfaces were pretreated with either a 37% phosphoric acid solution in water or a 70% nitric acid solution in water. Additional amalgam surfaces were left untreated (Run #1) for comparison. Tricure ionomer adhesive was applied to the treated or untreated surfaces in a powder:liquid ratio of 1.4:1 and then cured for 30 seconds. SCOTCHBOND Dual Cure adhesive and P-50™ composite were then sequentially applied to the coated ionomer surface as described in EXAMPLE 1.

Table 3 summarizes the results and illustrates that the oxidative pretreatment of nitric acid provides significantly improved adhesion relative to the non-oxidative phosphoric acid pretreatment or the untreated control.

TABLE 3

| Run # | Primer solution (concentration in water) | $E^O$ (Volts) | Powder: Liquid Ratio | Shear adhesive strength,[1] (MPa) |
|---|---|---|---|---|
| 1 | None | | 1.4:1 | 2.0 |
| 2 | Phosphoric Acid (37%) | -0.28 | 1.4:1 | 2.5 |
| 3 | Nitric acid (70%) | 0.94 | 1.4:1 | 5.9 |

[1]Mean of 6 samples.

EXAMPLE 4

Amalgam surfaces were pretreated with aqueous solutions of nitric acid (containing 0.0, 5.0, or 70.0 percent by weight nitric acid). Tricure ionomer adhesives were separately applied to the treated surfaces in three powder:liquid ratios (0.7:1, 1:1, and 1.4:1) as described in EXAMPLE 2. SCOTCHBOND™ Dual Cure adhesive and P-50™ composite were then sequentially applied to each cured ionomer surface as described in EXAMPLE 2. Set out in Table 4 are the run #, primer solution, the powder to liquid ratio of VITREBOND™ Glass Ionomer, and the mean shear adhesion value (in MPa).

The data shows that adhesion to set amalgam can be enhanced via pretreatment with aqueous nitric acid, that adhesion increases with increasing nitric acid concentration and that powder:liquid ratio appears to impact adhesion performance when a high concentration of nitric acid is present in the pretreatment. A similar effect was observed in Example 2.

TABLE 4

| Run # | Primer solution (concentration in water) | $E^O$ (Volts) | Powder: Liquid Ratio | Shear adhesive strength,[1] (MPa) |
|---|---|---|---|---|
| 1 | Water | — | 0.7:1 | 2.9 |
| 2 | Water | — | 1:1 | 3.1 |
| 3 | Water | — | 1.4:1 | 2.3 |
| 4 | Nitric acid (5%) | — | 0.7:1 | 5.6 |
| 5 | Nitric acid (5%) | 0.94 | 1:1 | 7.4 |
| 6 | Nitric acid (5%) | 0.94 | 1.4:1 | 6.7 |
| 7 | Nitric acid (70%) | 0.94 | 0.7:1 | 6.5 |
| 8 | Nitric acid (70%) | 0.94 | 1:1 | 12.3 |
| 9 | Nitric acid (70%) | 0.94 | 1.4:1 | 12.2 |

[1]Mean of at least 4 samples.

EXAMPLE 5

Amalgam surfaces were pretreated with aqueous solutions containing 0.0, 7.5, 15.0, or 30% hydrogen peroxide as previously described in EXAMPLE 1. Two adhesive systems were then evaluated for adhesion to the pretreated substrate. Either tricure ionomer (as described in PREPARATORY EXAMPLE 1) followed by SCOTCHBOND™ Dual Cure adhesive (hereinafter referred to as system "A");

or a dental primer followed by a dental adhesive (as described in PREPARATORY EXAMPLE 2 and hereinafter referred to as system "B") were applied to the amalgam surface. Each material was then exposed to a 40 or 20 second light exposure, respectively, using a VISILUX™ 2 dental curing lamp (3M). P-50™ composite was then applied as previously described.

Set out in Table 5 are the run #, the concentration of hydrogen peroxide in the pretreatment, $E^O$ oxidative of the oxidant (in Volts), adhesive system, and the mean shear adhesive strength of the samples evaluated. The data shows that the bond strengths increase with increasing hydrogen peroxide concentration for both adhesive systems and that slightly higher adhesion values are obtained with system B.

TABLE 5

| Run # | Primer solution (concentration in water) | $E^O$ (Volts) | Adhesive system | Shear adhesive strength,[1] (MPa) |
|---|---|---|---|---|
| 1 | Water | | A | 6.5 |
| 2 | Hydrogen peroxide (7.5%) | 1.77 | A | 7.1 |
| 3 | Hydrogen peroxide (15%) | 1.77 | A | 8.4 |
| 4 | Hydrogen peroxide (30%) | 1.77 | A | 9.6 |
| 5 | Water | | B | 9.1 |
| 6 | Hydrogen peroxide (7.5%) | 1.77 | B | 10.2 |
| 7 | Hydrogen peroxide (15%) | 1.77 | B | 10.5 |
| 8 | Hydrogen peroxide (30%) | 1.77 | B | 12.0 |

[1]Mean of at least 4 samples.

Various modifications and alterations of this invention will be apparent to those skilled in the art without departing from the scope and spirit of this invention, and it should be understood that this invention is not limited to the illustrative embodiments set forth herein.

What is claimed is:

1. A method for adhering to or coating a dental metal, comprising the steps of:
    applying to said dental metal adhesively effective amounts of a primer composition and an adhesive, wherein said primer composition comprises an oxidant having an $E^O$ oxidation potential greater than the absolute value of the $E^O$ reductant of said dental metal; and
    hardening said adhesive.

2. A method according to claim 1, wherein said primer and said adhesive are concurrently applied to said dental metal.

3. A method according to claim 1, wherein said primer further comprises a solvent, said oxidant has an $E^O$ at least 0.8 Volts, and said dental metal is a dental amalgam.

4. A method according to claim 3, wherein said oxidant has an $E^O$ between 0.8 Volts and 3 Volts.

5. A method according to claim 3, wherein said oxidant is selected from the group consisting of $NO_2-$, $NO_3-$, $ClO-$, $ClO_3-$, $ClO_4-$, $BrO-$, $BrO_3-$, $IO-$, $IO_3-$, $MnO_4-$, $Cr_2O_7-$, $S_2O_8^{-2}$, $Ru^{+4}$, $Cr^{+6}$, $Rh^{+4}$, $Ce^{+4}$, $Mn^{+3}$, $Co^{+3}$, $Cu^{+2}$, $ClO_2$, $Br_2$, $MnO_2$, and $H_2O_2$.

6. A method according to claim 3, wherein said oxidant is selected from the group consisting of $NO_3-$, $MnO_4-$, $Cr_2O_7-$, $S_2O_8^{-2}$, and $H_2O_2$, and wherein said method provides an average measured shear strength of at least 8 MPa between said adhesive and said dental metal.

7. A method according to claim 3, wherein said solvent is a polar solvent having a dielectric constant greater than or equal to 15, and wherein said method provides an average measured shear strength of at least 8 MPa between said adhesive and said dental metal.

8. A method according to claim 5, wherein said solvent is a polar solvent having a dielectric constant greater than 30.

9. A method according to claim 3, wherein said solvent is a polar solvent having a dielectric constant greater than 70.

10. A method according to claim 8, wherein said oxidant is present in said solvent in an amount between 0.1M and 15M.

11. A method according to claim 3, wherein said oxidant is present in said solvent in an amount between 1M and 12M.

12. A method according to claim 8, wherein said primer contains between 20 and 95 percent solvent.

13. A method according to claim 8, wherein said primer contains between 30 and 95 percent solvent.

14. A method according to claim 3, wherein said adhesive contains one or more compounds selected from the group consisting of monomers, oligomers, and polymers, and wherein said adhesive is capable of forming a hardenable film on the surface of said dental metal.

15. A method according to claim 14, wherein said adhesive compounds contain one or more ethylenically unsaturated addition polymerizable substances.

16. A method according to claim 14, wherein said adhesive contains one or more compounds selected from the group consisting of monofunctional or polyfunctional acrylates and methacrylates, acrylamides and methacrylamides, vinyl compounds, and styrene compounds.

17. A method according to claim 7, wherein said adhesive is applied to said dental metal in one or more layers and wherein at least one layer comprises a water-based cement.

18. A method according to claim 17, wherein said water-based cement is a glass ionomer cement.

19. A method according to claim 18, wherein said glass ionomer cement is applied to the dental metal prior to the application of a second adhesive composition and wherein said glass ionomer cement comprises ethylenically unsaturated groups which are capable of free radical crosslinking.

20. A method according to claim 9, wherein said method provides an average measured shear strength of at least 10 MPa between said adhesive and said dental metal.

21. A kit for adhering to or coating dental amalgam, comprising: a primer comprising an oxidant having an $E^O$ oxidation potential greater than 0.8 Volts; and an adhesive, wherein upon hardening said adhesive is capable of providing an average measured shear strength of at least 7 MPa between said adhesive and dental amalgam.

22. A kit according to claim 21, wherein said primer further comprises a polar solvent having a dielectric constant greater than or equal to 15.

23. A kit according to claim 22, wherein said oxidant is selected from the group consisting of $NO_2-$, $NO_3-$, $ClO-$, $ClO_3-$, $ClO_4-$, $BrO-$, $BrO_3-$, $IO-$, $IO_3-$, $MnO_4-$, $Cr_2O_7-$, $S_2O_8^{-2}$, $Ru^{+4}$, $Cr^{+6}$, $Rh^{+4}$, $Ce^{30\ 4}$, $Mn^{+3}$, $Co^{+3}$, $Cu^{+2}$, $ClO_2$, $Br_2$, $MnO_2$, and $H_2O_2$.

24. A kit according to claim 22, wherein said oxidant is selected from the group consisting of $NO_3-$, $MnO_4-$, $Cr_2O_7-$, $S_2O_8^{-2}$, and $H_2O_2$, and wherein said kit is capable of providing an average measured shear strength of at least 10 MPa between said adhesive and said dental metal.

25. A kit according to claim 23, wherein said solvent is a polar solvent having a dielectric constant greater than 30.

26. A kit according to claim 22, wherein said oxidant is present in said solvent in an amount between 1M and 12M.

27. A kit according to claim 22, herein said primer contains between 20 and 95 percent solvent.

28. A kit according to claim 23, wherein said primer contains between 30 and 95 percent solvent.

29. A kit according to claim 23, wherein said adhesive contains one or more compounds selected from the group consisting of monomers, oligomers, and polymers, and wherein said adhesive compounds contain one or more ethylenically unsaturated addition polymerizable substances.

30. A kit according to claim 23, wherein said adhesive contains one or more compounds selected from the group consisting of monofunctional or polyfunctional acrylates and methacrylates, acrylamides and methacrylamides, vinyl compounds, and styrene compounds.

31. A kit according to claim 21, wherein said adhesive is suitable for application to said dental metal in one or more layers and wherein at least one layer comprises a glass ionomer cement.

32. A kit according to claim 31, wherein said glass ionomer cement comprises ethylenically unsaturated groups which are capable of free radical crosslinking.

33. An adhesive composition, comprising: a primer comprising an oxidant having an $E^O$ oxidation potential greater than 0.8 Volts, wherein said oxidant is selected from the group consisting of $NO_2-$, $NO_3-$, $ClO-$, $ClO_3-$, $ClO_4-$, $BrO-$, $BrO_3-$, $IO-$, $IO_3-$, $MnO_4-$, $Cr_2O_7-$, $S_2O_8^2$, $Ru^{+4}$, $Cr^{+6}$, $Rh^{+4}$, $Ce^{+4}$, $Mn^{+3}$, $Co^{+3}$, $Cu^{+2}$, $ClO_2$, $Br_2$, $MnO_2$, and $H_2O_2$; and an adhesive, wherein upon hardening said adhesive is capable of providing an average measured shear strength of at least 7 MPa between said adhesive and dental amalgam.

34. An adhesive composition according to claim 33, wherein said primer further comprises between 20 and 95 percent solvent of a polar solvent having a dielectric constant greater than 30.

35. An adhesive composition according to claim 33, wherein said oxidant is selected from the group consisting of $NO_3-$, $MnO_4-$, $Cr_2O_7-$, $S_2O_8^{-2}$, and $H_2O_2$, and wherein said kit is capable of providing an average measured shear strength of at least 10 MPa between said adhesive and said dental metal.

36. An adhesive composition according to claim 33, wherein said adhesive contains one or more compounds selected from the group consisting of monomers, oligomers, and polymers, and wherein said adhesive compounds contain one or more ethylenically unsaturated addition polymerizable substances.

37. An adhesive composition according to claim 36, wherein said adhesive contains one or more compounds selected from the group consisting of monofunctional or polyfunctional acrylates and methacrylates, acrylamides and methacrylamides, vinyl compounds, and styrene compounds.

38. An adhesive composition according to claim 37, wherein said adhesive is suitable for application to said dental metal in one or more layers and wherein at least one layer comprises a glass ionomer cement.

* * * * *

UNITED STATES PATENT AND TRADEMARK OFFICE
CERTIFICATE OF CORRECTION

PATENT NO. : 5,849,813
DATED : December 15, 1998
INVENTOR(S) : Joel D. Oxman

It is certified that error appears in the above-identified patent and that said Letters Patent is hereby corrected as shown below:

Column 19, claim 5,
Line 54, "$S_2O_8^{-2}$—" should read -- $S_2O_8^{-2}$ --.

Column 20, claim 23,
Line 51, "$Cr_{20}O_7$—, $S_2O_8^{-2}$ —should read -- $Cr_2O_7$— $S_2O_8^{-2}$ --.

Column 20, claim 27,
Line 62, "claim 22 herein" should read -- claim 22, wherein --.

Column 21, claim 33,
Line 22, "$S_2O_8^{2}$" should read -- $S_2O_8^{-2}$ --.

Signed and Sealed this

Eighteenth Day of September, 2001

Attest:

NICHOLAS P. GODICI
*Attesting Officer*    *Acting Director of the United States Patent and Trademark Office*